United States Patent [19]
af Ekenstam et al.

[11] Patent Number: 4,695,576
[45] Date of Patent: Sep. 22, 1987

[54] L-N-N-PROPYLPIPECOLIC ACID-2,6-XYLIDIDE

[75] Inventors: Bo T. af Ekenstam, Hjalteby; Christer Bovin, Frolunda, both of Sweden

[73] Assignee: Astra Lake Medel Aktiebolag, Sodertalje, Sweden

[21] Appl. No.: 785,819

[22] Filed: Oct. 9, 1985

Related U.S. Application Data

[63] Continuation-in-part of Ser. No. 629,738, Jul. 9, 1984, abandoned, which is a continuation of Ser. No. 377,104, May 11, 1982, abandoned.

[51] Int. Cl.$^4$ .................. C07D 211/60; A61K 31/445
[52] U.S. Cl. .................................... 514/330; 546/225; 514/817; 514/818
[58] Field of Search ................ 546/225; 514/330, 817, 514/818

[56] References Cited

U.S. PATENT DOCUMENTS

| | | | |
|---|---|---|---|
| 2,799,679 | 7/1957 | Ekenstam et al. | 546/225 |
| 4,110,331 | 8/1978 | Pettersson | 546/225 |
| 4,302,465 | 11/1981 | Ekenstam et al. | 546/225 |

FOREIGN PATENT DOCUMENTS

| | | |
|---|---|---|
| 775749 | 5/1957 | United Kingdom . |
| 775750 | 5/1957 | United Kingdom . |
| 800565 | 8/1958 | United Kingdom . |
| 824542 | 12/1959 | United Kingdom . |
| 869978 | 6/1961 | United Kingdom . |
| 949729 | 2/1964 | United Kingdom . |

OTHER PUBLICATIONS

Luduena, F. P., *Annual Review of Pharmacology*, "Duration of Local Anaesthesia", 9, 503–520 (1969).
Tullar, B. F., *J. Med. Chem.*, "Optical Isomers of Mepivacaine and Bupivacaine", 14, 891–892 (1971).
Friberger, P. et al., *Acta Pharm. Suecica*, "Some Physicochemical Properties of The Racemates and The Optically Active Isomers of Two Local Anaesthetic Compounds", 8, 361–364 (1971).
Aberg, G., *Acta Pharmacol et Toxicol*, "Toxicological and Local Anaesthetic Effects of Optically Active Isomers of Two Local Anaesthetic Compounds", 31, 273–286 (1972).
Af Ekenstam, B., et al., *Acta Chemica Scandinavica*, "Local Anaesthetics I. N-Alkyl Pyrrolidine and N-Alkyl Piperidine Carboxylic Acid Amides", 11, 1183–1190 (1957).
Aberg, G., et al., *Acta Pharmacol. et Toxicol*, "Studies on The Duration of Local Anaesthesia: Structure/Activity Relationships in a Series of Homologous Local Anaesthetics", 41, 432–443 (1977).
Aberg, G., *Linkoping University Medical Dissertations*, "Studies on Mepivacaine and its Optically Active Isomers with Special Reference to Vasoactive Properties", No. 5, pp. 1–32 (1972).

*Primary Examiner*—Norma S. Milestone
*Attorney, Agent, or Firm*—Seidel, Gonda, Goldhammer & Abbott

[57] ABSTRACT

The local anesthetic, L-N-n-propylpipecolic acid-2,6-xylidide, namely:

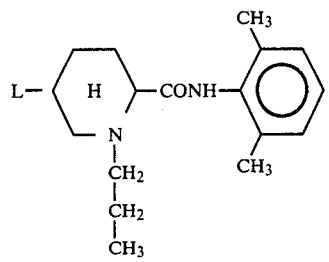

This compound is prepared by chlorinating L-pipecolic acid to yield the acid chloride, namely L-pipecolic acid chloride. The acid chloride is then reacted with 2,6-xylidine to yield L-pipecolic acid-2,6-xylidide. The L-N-pipecolic acid-2,6-xylidide is then propylated to yield the L-N-n-propylpipecolic acid-2,6-xylidide, which is a potent local anesthetic for humans and is of relatively low toxicity.

6 Claims, No Drawings

L-N--N-PROPYLPIPECOLIC ACID-2,6-XYLIDIDE

BACKGROUND OF THE INVENTION

This application is a continuation-in-part of copending application Ser. No. 629,738 filed July 9, 1984, now abandoned, which is in turn a continuation of application Ser. No. 377,104 filed May 11, 1982, now abandoned.

A large variety of N-alkyl-pipecolic acid amides have been synthesized. A number of these compounds have found use as local anesthetics, such as Mepivacaine, namely the racemate of N-methylpipecolic-acid-2,6-xylidide:

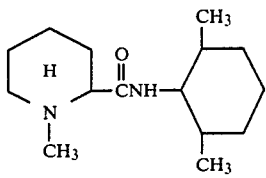

and Bupivacaine, namely the racemate of N-butyl-pipecolicacaid-2,6-xylidide:

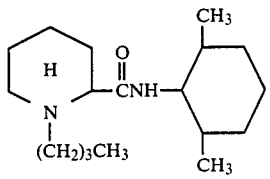

References disclosing homologs of this series of compounds include U.S. Pat. No. 2,799,679; British Pat. Nos. 775,749; 755,750; 800,565; 824,542; 869,978; 949,729; U.S. Pat. Nos. 4,110,331; and 4,302,465.

There is a summary paper dealing with these types of anesthetics, and related compounds in a paper in *Acta Chemica Scandinavica II*, (1957) No. 7 pp. 1183–1190 by Bo Thuresson af Ekenstam et al.

There is a discussion of the effect of optical isomers in related compounds in *J. Med. Chem.*, 14 (1971) pp. 891–892 entitled "Optical Isomers of Mepivacaine And Bupivacaine" by Benjamin F. Tullar; *Acta Pharm. Suecica*, 8 (1971) pp. 361–364 entitled "Some Physicochemical Properties of the Racemates And The Optically Active Isomers Of Two Local Anaesthetic Compounds", by P. Friberger et al.; *Acta Pharmacol et Toxicol*, 31 (1972) pp. 273–286 entitled "Toxicological And Local Anaesthetic Compounds", by G. Aberg; *Annual Review of Pharmacology*, 9 (1969) pp. 503–520 entitled "Duration of Local Anaesthesia", by F. P. Luduena and *Acta Pharmacol. et Toxicol*, 41 (1977) pp. 432–443 entitled "Studies On The Duration Of Local Anaesthesia: Structure/Activity Relationships In A Series Of Homologous Local Anaesthetics", by G. Aberg et al.

SUMMARY OF THE INVENTION

We have found that L-N-n-propylpipecolic acid-2,6-xylidide is markedly superior as a local anesthetic for humans to other known homologues of these compounds including the commercially exploited local anesthetics Mepivacaine, which is the N-methyl homolog, and Bupivacaine, which is the N-n-butyl homolog. This is surprising because the analgesic activity of the racemic n-propyl compound (R-N-n-propylpipecolic acid-2,6-xylidide) is so far below that of the racemic Bupivacaine (R-N-n-butylpipecolic acid-2,6-xylidide) as to stultify any further research on the n-propyl compound. Furthermore, research on the optical isomers of Mepivacaine and Bupivacaine reveal that the differences in potency compared to the racemate were not of such magnitude as to justify the commercial production of the optical isomers.

The effect of modifying the alkyl group on the nitrogen atom in the piperidine ring of this family of homologs is not completely understood. However, it is clear that any alkyl group of five or more atoms on this nitrogen atom is too toxic to function as a local anesthetic.

We have discovered that the laevo optical stereoisomer N-n-propylpipecolic acid-2,6-xylidide has optimal properties as a local anesthetic.

Our method of preparing L-N-n-propylpipecolic acid-2,6-xylidide comprises resolving pipecolic acid to isolate the laevo optical stereoisomer. The laevo pipecolic acid hydrochloride is then chlorinated to form a laevo pipecolic acid chloride hydrochloride:

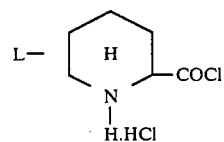

The acid chloride hydrochloride is then reacted with 2,6-xylidine to form the L-pipecolic acid-2,6-xylidide hydrochloride:

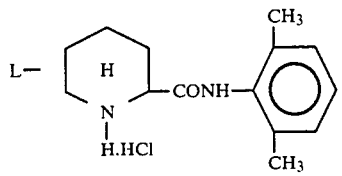

L-pipecolic acid-2,6-xylidide is then propylated to yield the L-N-n-propylpipecolic acid-2,6-xylidide.

DETAILED DESCRIPTION OF THE PREFERRED EMBODIMENT

The following illustrative process described in four steps may be used to prepare the L-N-n-propylpipecolic acid-2,6-xylidide:

EXAMPLE 1

RESOLUTION OF PIPECOLIC ACID 130 grams of pipecolic acid and 158.6 grams of Laevo (+)-tartaric acid are dissolved under stirring in 2,000 ml 95% ethyl alcohol and 125 ml water at a temperature of approximately 80° C. The solution is allowed to cool to room temperature and after two days the crystallized D-pipecolic-tartrate is separated. The L-pipecolic-tartrate remains in solution.

The filtrate is evaporated and dissolved in 5% acetic acid. Finally the solution is treated with Amberlite IR 45* in an ion exchanger. The eluate thus obtained is evaporated and the resulting crystalline residue is dried with potassium hydroxide in vacuo. The product obtained consists of L-pipecolic acid $[\alpha]^{24}_D$ $-26.2°(C=5**, H_2O)$.

*A commercial weakly basic polystyrene-polyamine anion exchange resin sold by Rohm & Haas Company of Philadelphia, Pa. designed primarily to remove strong acids.
**C means concentration in grams per 100 ml of solution.

EXAMPLE 2

PREPARATION OF L-PIPECOLIC ACID CHLORIDE HYDROCHLORIDE

The chlorination of the L-pipecolic acid hydrochloride is achieved by adding during a time period of 15–20 minutes four grams of phosphorus pentachloride to a suspension of four grams of L-pipecolic acid hydrochloride in 40 ml acetylchloride. The initial reaction is effected at a temperature of about 35° C. under stirring for a time duration of two hours. The chlorination is completed by adding during a time period of about 10 minutes an additional two grams of phosphorus pentachloride and stirring over a further period of four hours while maintaining the suspension at a temperature of about 35° C.

The resulting L-pipecolic acid chloride hydrochloride is filtered and washed with toluene and acetone. The crystalline residue is then dried in vacuo. The product starts to sinter at 140° C. (using a microscope) then decomposes at 150° C. and all is melted at 155° C.

EXAMPLE 3

PREPARATION OF L-PIPECOLIC ACID-2,6-XYLIDIDE

A mixture of 2.7 ml 2,6-xylidine, 4 ml acetone, and 4 ml N-methylpyrrolidone is gradually added under stirring for two hours at a temperature of approximately 70° C. to a suspension of 4 grams of L-pipecolic acid chloride hydrochloride. This yields a crystalline product, which is filtered, washed with acetone and dried. This crystalline product is then dissolved in water and the base is precipitated by the addition of ammonia.

The base is then extracted by the use of toluene and is recovered by evaporation. The base is recrystallized from a mixture of hexane and ethanol to yield L-pipecolic acid-2,6-xylidide. The melting point of this compound is 129°–130° C., $[\alpha]^{25}D$ +46.4° (C=2, 1 M HCl).

EXAMPLE 4

PREPARATION OF L-N-n-PROPYLPIPECOLIC ACID 2,6-XYLIDIDE 7.9 ml n-propylbromide and 6.8 grams of potassium carbonate are added to a solution of 17 grams of L-pipecolic acid-2,6-xylidide dissolved in 60 ml of isopropyl alcohol. Thereafter, 5 ml of water is added to the mixture and the reaction is carried out for a period of about four hours at approximately 72° C.

To complete the reaction, a further 0.8 ml n-propylbromide are added under continuous stirring and heating for 4 hours. The residue is treated with a mixture of 250 ml toluene and an equal amount of water under gentle heating at approximately 50° C. The toluene layer is separated and washed three times with 100 ml warm water (40° C.). A 175 ml portion of the toluene is removed by evaporation and the remainder is stored in a refrigerator at +5° C. for 6 hours to achieve crude crystalline L-N-n-propylpipecolic acid-2,6-xylidide. The crystalline product is separated by filtration, washed with some cooled toluene and dried at 70° C.

Approximately 16 grams of crude L-N-n-propylpipecolic acid-2,6-xylidide are obtained. Recrystallization from toluene gives approximately 14 grams of the pure product, m.p. 144°–146° C., $[\alpha]^{25}D$ −82.0°(C=2, MeOH).

This product is dissolved in 100 ml ethanol and neutralized with concentrated hydrochloric acid.

Ethanol is removed by evaporation and the hydrochloride product obtained is vacuum dried. Finally the latter is recrystallized from 75 ml isopropyl alcohol. The yield is approximately 12 grams of L-N-n-propylpipecolic acid-2,6-xylidide hydrochloride, m.p. 260°–262° C., $[\alpha]^{25}D$ −6.6°(C=2, H$_2$O).

The reactions for achieving the compound of the present invention may be shown diagrammatically (commencing with L-pipecolic acid hydrochloride):

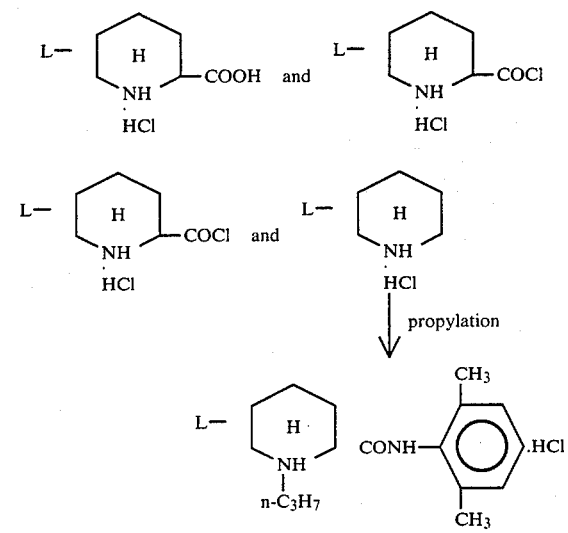

Useful background information concerning the synthesis of the homologs of N-alkyl-pipecolic acid-2,6-xylidide is contained in British Pat. Nos. 775,750; 775,749; 824,542; 800,565 and 949,729; and in the article by Ekenstam et al. in *Acta Chem. Scand.* 11 (1957) No. 7, pp. 1183–1190, the disclosures of which are incorporated by reference.

A toxicological-pharmacological evaluation of the compound of the present invention, and related homologs is set forth below.

The toxicity of the homologous series of N-alkyl-pipecolic acid-2,6-xylidides increases step wise and quickly with the lengthening of the alkyl chain. This is manifest from Table 1 set forth below, which compares racemic mixtures of alkyl homologues having from 1 to 5 carbon atoms.

TABLE 1

| | TOXICOLOGICAL DATA | | | |
|---|---|---|---|---|
| No. | Structure (Racemate) | Molecular Weight | Tissue lacking in toxicity limits in % | LD$_{50}$** I.v. (intravenous) mg/kg/mouse |
| 1 | N—methylpipecolic acid-2,6-xylidide | 246.46 | 3.5 | 40.3 |
| 2 | N—ethylpipecolic acid-2,6-xylidide | 260.17 | 3.0 | 21.0 |
| 3 | N—n-propylpipecolic acid 2,6-xylidide | 274.18 | 1.5 | 13.6 |
| 4 | N—n-butylpipecolic acid-2,6-xylidide | 288.19 | 0.75 | 7.8 |
| 5 | N—n-pentylpipecolic acid-2,6-xylidide | 302.20 | slightly soluble in water and tissue | |

TABLE 1-continued
TOXICOLOGICAL DATA

| No. | Structure (Racemate) | Molecular Weight | Tissue lacking in toxicity limits in % | $LD_{50}$** I.v. (intravenous) mg/kg/mouse |
|---|---|---|---|---|
| | | | | irritating*** |

*Trypan blue test: Hoppe et al. (1950), 39, 147–151 "Use of Trypan Blue and Rabbit Eye Tests For Irritation", J. Amer. Pharm. Assoc. (Scient. Ed.), the values are approximate threshold values of tissue irritancy.
**$LD_{50}$, i.e. 50% mortality of mice.
***Studies On The Duration Of Local Anaesthesia: Structure/Activity Relationships In A Series Of Homologous Local Anaesthetics, by G. Aberg, et al., Acta pharmacol. et toxicol., 41 (1977) pp. 432–443, Table 1 at p. 435.

From Table 1 it can be seen that the toxicological effects of the subject homologous series increases stepwise and quickly when the N-alkyl chain is lengthened, both with regards to tissue toxicity limits as well as intravenous toxicity.

The optical stereoisomers of the substances Nos. 1, 2 and 4 in Table 1 have earlier been prepared in a pure form. These products have also earlier been shown to give insignificant differences with regards to the parameters which are of vital importance for the clinical use of an anesthetic product. See study which involves the discussed substances according to Table 1, by G. Aberg et al, "Studies on the Duration of Local Anesthesia: Structure/Activity Relationship in a Series of Homologous Local Anesthetics", Acta Pharmacol. et Toxicol. 41 (1977) pp. 432–443.

Some of the pure stereoisomers, whose structures are referred to in Table 2, have, on repeated occasions, been studied with regards to possible important differences of their practical anesthesiological importance. Among others, substance No. 1 in Table 1, has been studied by G. Aberg: Studies on Mepivacaine and its Optically Active Isomers with Special Reference to Vasoactive Properties, Dept. of Pharmacology, School of Medicine, Linkoping, Sweden, 1972.

According to this work, no great differences in effect can be expected between the different stereoisomers in the homologous group starting with Mepivacaine (the N-methyl compound).

The stereoisomers of the substances Nos. 1, 2 and 4, (Table 2) have been prepared earlier in a pure form but have shown no significant clinical differences in humans with respect to their use as local anesthetics. According to the invention, the L-isomer of substance No. 3 has now been prepared in a pure form and the results of studies on intracutaneous wheals as well as finger blockades in humans have shown that this compound has surprisingly good properties.

By use of intracutaneous wheals it is possible to measure the analgesic effect of an anesthetic on the peripheral nerve endings of the epidermis.

This technique gives information about:
(1) The duration of anesthesia.
(2) Epidermal diffusion.
(3) Vascular effects.

TABLE 2
INTRACUTANEOUS WHEALS[1]

| Substance | | Molecular weight base | Melting points HCl-salts °C | Opt. activity | | Analgesia-duration | |
|---|---|---|---|---|---|---|---|
| No. | Form* | | | System | $[\alpha]_D^{25\circ}$ | Conc. % | Minutes |
| 1 | L | 246.16 | 293–95 | C = 5** | −63 | 0.5 | 68 ± 11 |
| | R | | 260–62 | MeOH | 0 | " | 65 ± 9 |
| | D | | 293–95 | | +63 | " | 53 ± 8 |
| 2 | L | 260.17 | 255 | C = 2 | −70 | 0.25 | 76 ± 11 |
| | R | | 252–54 | EtOH | 0 | " | 63 ± 13 |
| | D | | 255 | | +69.5 | " | 58 ± 11 |
| 3 | L | 274.18 | 260–62 | C = 2 | −82 | 0.25 | 220 ± 23*** |
| | R | | 260.5 | MeOH | 0 | " | 84 ± 15 |
| | D | | 260–62 | | +82 | " | 81 ± 14*** |
| 4 | L | 288.19 | 255–57 | C = 2 | −80.9 | 0.25 | 76 ± 10 |
| | R | | 255–56 | MeOH | 0 | " | 118 ± 15 |
| | D | | 255–57 | | +80.9 | " | 75 ± 11 |
| 5 | L | | Not usable as slightly soluble in water, irritating | | | | |
| | R | | | | | | |
| | D | | | | | | |

[1] Infiltration anesthesia on forearms of man. The test solutions were injected intracutaneously on the dorsum of the forearms of 12 healthy volunteers, 20–25 years old. Three wheals were made on each arm in a rotating system in a double-bind fashion. The local anesthetic effect was tested using a pin-prick technique. The "duration of anesthesia" was defined as the time during which none out of six pin-pricks into the wheal was felt. The method has been described by Dhuner et al. (1972). Dhuner, K.G., D.H. Lewis, A. Nyquist, D.Selander & E.Stig: Vascular effects of the isomers of mepivacaine, Acta Anaest. Scand. 1972, Suppl. 48, 45–52.
*L = Laevo, R = Racemic, D = Dextro
**C equals grams per 100 ml of solution.
***New isolated stereoisomers

TABLE 3
RESULTS OF THE FINGER BLOCKADE[2]

| Substance | | Concentration % | Time of onset minutes* | Analgesia-duration minutes | Frequency** |
|---|---|---|---|---|---|
| No. | Form | | | | |
| 1 | L | 1.0 | 7 ± 3 | 124 ± 21 | 11/12 |
| | R | " | 7 ± 2 | 102 ± 22 | 13/13 |
| | D | " | 7 ± 2 | 71 ± 13 | 9/13 |
| 2 | L | 0.5 | 9 ± 2 | 141 ± 18 | 11/13 |
| | R | " | 10 ± 1 | 123 ± 19 | 12/12 |
| | D | " | 9 ± 3 | 112 ± 21 | 10/13 |
| 3 | L | 0.25 | 12 ± 2 | 739 ± 46*** | 6/7 |

TABLE 3-continued

RESULTS OF THE FINGER BLOCKADE[2]

| Substance | | | Time of onset | Analgesia-duration | |
|---|---|---|---|---|---|
| No. | Form | Concentration % | minutes* | minutes | Frequency** |
| | R | " | 10 ± 1 | 263 ± 31 | 9/10 |
| | D | " | 14 ± 3 | 175 ± 21*** | 7/8 |
| 4 | L | 0.25 | 13 ± 3 | 259 ± 37 | 13/20 |
| | R | " | 9 ± 2 | 388 ± 50 | 15/20 |
| | D | " | 15 ± 4 | 243 ± 38 | 14/20 |
| 5 | | | Not usable, too irritating against tissue | | |

[2]Digital nerve blocks in man. The test solutions were injected to block the ulnar volar nerves on the 2nd and 4th fingers of the samevolunteers who had participated in the intracutaneous wheal tests described above. The tests were carried out in a double blind fashion in a rotating system, so that each solution was used with equal frequency on each of the blocked fingers. A total of for injections 1.0 ml per injection, was done in each subject. One week later the procedure was repeated in the same subjects using the remaining test solutions. This method has been described by Dhuner et al. (1972) (for citation see Table 2 footnote 1). To measure the efficacy and duration of the blocks, the individual fingers were pricked rapidly 10 times with a needle algesimeter and the number of painful pricks noted. Each finger was tested every five minutes until complete recovery. The time of complete anesthesia has been called "duration of anesthesia".
*i.e. - the time from injection to complete analgesia
**i.e. - the number of successful anesthesias of total number of anesthesias performed (no anesthesia is possible if the ulnar volar nerves are not contacted by the anesthetic).
***new isolated steroisomers.

When comparing the results of intracutaneous wheal (Table 2) and finger-blockade (Table 3) it can be seen that of the 12 optically active and inactive structures, substance No. 3, namely L-N-n-propylpipecolic acid-2,6-xylidide, gives the optimal increase of anesthetic effects. This unexpected increase in effect runs contra to what would be expected from the activity of prior stereoisomers. Indeed, with substance No. 4, the racemic mixture provides significantly longer duration of analgesia than the corresponding D and L isomers.

Referring to Table 2, of the methyl to butyl stereoisomers and racemates (the amyl isomers are not usable), without exception the methyl, ethyl and butyl L and D isomers have activity within the overlapping area of experimental error. With the methyl and the ethyl isomers, all three forms have similar activity within the experimental error. With the butyl isomer, the optically active forms have almost identical activity, with the racemate being more active. Similar results are shown in Table 3.

Until now, racemic Bupivacaine, namely No. 4 R, has been the compound having the largest clinical use in this series. During the past 15 years Bupivacaine has had a world wide increase in clinical use. As the above data discloses the L-N-n-propylpipecolic acid-2,6-xylidide has double the activity of R-Bupivacaine and is strikingly superior to Bupivacaine, being both a far better anesthetic and much less toxic.

In order to give a better illustration of the differences in effect, a series of various intracutaneous wheals has been investigated with regards to the skin temperature within the wheals during anesthesia. Based on this investigation, interesting differences in the temperatures can be observed.

Equipment used for the temperature measurements
(experimental)

The given values have been registered 10 minutes after the intracutaneous injection, and thereafter the control values were immediately determined.

The mean value of 6 wheals for each substance forms the basis for the values. The control values, however, represent the mean value obtained from 4 different sites measured outside the wheals 90 degrees apart and 2 centimeters from the wheal's center.

In the temperature measurements, an Oriel temperature apparatus* has been used. This is battery driven and is connected to a detector (diameter, 2.5 mm) and has an accuracy of ±0.1° C. The temperature of the skin is measured by pressing the detector against the skin with a pressure of 100 grams. It is retained against the skin until a constant temperature is obtained.
*A widely used apparatus to measure skin temperature.

In Table 4, $T_1$ is the measurement obtained at the center of the wheal, and $T_2$ is the average of four measurements taken 90 degrees apart outside of the wheal and within 2 centimeters of the wheal's center.

TABLE 4

TEMPERATURE MEASUREMENTS, ACCURACY: +0.1° C.

| No. | Substance as HCl-salt | Conc.% | $T_1$ °C. Intracutaneous Wheal | $T_2$ °C. Controls | °C. Difference |
|---|---|---|---|---|---|
| 1 | Lidocaine | 1.0 | 30.2 | 29.3 | +0.9 |
| 2 | Lidocaine + adrenaline* 1:200000 | 1.0 | 27.8 | 28.9 | −1.1 |
| 3 | R—Bupivacaine | 0.25 | 31.5 | 32.1 | −0.6 |
| 4 | L-N—n-propyl pipecolic acid-2,6-xylidide | 0.25 | 30.0 | 31.2 | −1.2 |
| 5 | R—N—n-propyl-pipecolic acid-2,6-xylidide | 0.25 | 33.1 | 33.2 | −0.1 |
| 6 | R—N—2-hydroxy-ethyl-pipecolic | 1.0 | 31.2 | 30.7 | +0.5 |

TABLE 4-continued

| | | TEMPERATURE MEASUREMENTS, ACCURACY: +0.1° C. | | |
|---|---|---|---|---|
| No. | Substance as HCl-salt | Conc.% | $T_1$ °C. Intracutaneous Wheal | $T_2$ °C. Controls | °C. Difference |
| | acid-2,6-xylidide | | | | |

*Adrenaline (epinephrine) is a vasoconstrictor which reduces the cross-section of the wheal region's blood vessels and retains the Lidocaine in the wheal region.

From Table 4 it is seen that example No. 4, namely L-N-n-propylpipecolic acid-2,6-xylidide surprisingly lowers the temperature over its wheal to approximately the same extent as the combination of lidocaine with adrenaline (Table 4, example No. 2). This may be due to an effect on the blood vessels with the wheal similar to that of bdrenaline. The racemic compound of example No. 5 showed practically no change in temperature.

Tables 1–4 demonstrate the connection between L-N-n-propylpipecolic acid-2,6-xylidide and the most important parameters in each table, e.g. optical stereoisomer, duration of analgesia in intracutaneous wheals, the analgesic duration of fingerblocks, and the maximization of temperature decrease. It is manifest that L-N-n-propylpipecolic acid-2,6-xylidide is the optimal anesthetic within this homologous series.

Further biological tests

One commonly used anesthetic, bupivacaine, is reported to be cardiotoxic, especially in obstetrical use. As a result, new guidelines for testing cardiotoxicity of local anesthetics in man have been developed according to which new local anesthetics will be compared with bupivacaine.

In order to study the cardiotoxicity of L-N-n-propylpipecolic acid-2,6-xylidide (LEA) in comparison with other local anesthetics on the market, namely, N-n-butylpipecolic acid-2,6-xylidide (bupivacaine), and 2-diethylamino-2',6'-acetoxylidide (lidocaine) the following tests have been carried out. Lidocaine was chosen as a comparative substance as it has been documented to show no cardiotoxicity. The local anesthetic effect is, however, too short for epidural use.

Heart-toxicity in conscious rats

Materials and Methods

Male Sprague Dawley rats weighing 290–360 grams were prepared with intravenous catheters under local anesthesia using prilocaine (Citanest*) one hour before experiments. Rapid intravenous bolus injections over 5.0 seconds were given to groups of 8 rats, with a single injection to each animal. Bupivacaine and LEA were given in doses of 5, 7, 10, 14 and 20 μmol/kg and in addition LEA was given in 28 μmol/kg and lidocaine was given in doses of 14, 20, 28, 40 and 56 μmol/kg. The ECG was recorded on a Mingograf 34. Convulsions were recorded manually with an electronic marker on one channel of the Mingograf. Only "primary" arrhythmias occurring during the first 60 seconds have been analyzed to avoid confusion with late arrhythmias occurring secondary to respiratory arrest or cardiovascular collapse.

TABLE 5

| | Atrioventricular block | | |
|---|---|---|---|
| Dose umol/kg | Bupivacaine | LEA | Lidocaine |
| 5 | 0/8* | 0/8 | |
| 7 | 3/8 | 0/8 | |
| 10 | 6/8 | 2/8 | |
| 14 | 7/8 | 0/8 | 0/8 |
| 20 | 8/8 | 5/8 | 0/8 |
| 28 | | 8/8 | 3/8 |
| 40 | | | 4/8 |
| 56 | | | 8/8 |

*No. of rats responding/total no. of rats

TABLE 6

| | Ventricular arrhythmias | | |
|---|---|---|---|
| Dose umol/kg | Bupivacaine | LEA | Lidocaine |
| 5 | 0/8* | 0/8 | |
| 7 | 1/8 | 0/8 | |
| 10 | 5/8 | 2/8 | |
| 14 | 7/8 | 1/8 | 0/8 |
| 20 | 8/8 | 5/8 | 0/8 |
| 28 | | 8/8 | 0/8 |
| 40 | | | 2/8 |
| 56 | | | 1/8 |

*No. of rats responding/total no. of rats

Results and Comments

Most arrhythmias were transient lasting 0.2–4 seconds. Tables 5 and 6 show sustained arrhythmias (>5 seconds). Bupivacaine was the most potent and lidocaine the least potent to induce atrioventricular conduction disturbances.

Effect of intracoronary administration of LEA, lidocaine and bupivacaine

Materials and Methods

Eight pigs weighing around 50 kg were anesthetized with a continuous infusion of pentobarbital at 600 mg/h. Ventilation was established via a tracheotomy with 30% oxygen in nitrogen and normoventilation by a Siemens-Elema Servoventilator 900B. The following catheters were inserted after cutdown: Left ventricular, aortic, pulmonary arterial, great cardiac venous, left anterior descending coronary, arterial and central venous. Bupivacaine (B), lidocaine (L) and LEA were administered randomly in a dose response manner with dosages adjusted according to the agents' anesthetic potency. The potency ratio for bupivacaine:lidocaine is 4:1, and the potency ratio for LEA:lidocaine is 3:1. Lidocaine doses used were: 1, 2, 4, 8 and 16 mg. The corresponding doses for bupivaciane were 0.25, 0.5, 1, 2 and 4 mg and for LEA 0.33, 0.66, 1.33, 2.66 and 5.33 mg. The injection rate was adjusted according to the preinjection coronary blood flow. Each series of drug injections was preceded by a placebo infusion. Total hemodynamic and electrocardiographic recovery was allowed between doses and there was a one hour resting period between drugs.

Central pressures, left ventricular dP/dT and a complete chest lead ECG were recorded continuously. Cardiac output and great cardiac venous blood flow were determined before and directly after each dose of the local anesthetic agent.

TABLE 7

| Animal No. | 1st Dose | 2d Dose | 3d Dose | Outcome |
|---|---|---|---|---|
| 1 | L | B | LEA | Survived |
| 2 | B | L | LEA | Survived |
| 3 | L | B | LEA | Survived |
| 4 | LEA | L | B | VF 33 sec after 4 mg B |
| 5 | L | LEA | B | Survived |
| 6 | L | LEA | B | VF 1 sec after 4 mg B |
| 7 | LEA | L | B | Survived |
| 8 | LEA | B | L | Survived |

Comments

Six of the animals survived the study. Two animals died in ventricular fibrillation (from which they could not be resuscitated) within 33 sec from the end of the intracoronary injection of 4 mg of bupivacaine (Table 7).

Thus, the same kind of sudden cardiac collapse, which has led to the new guidelines for testing cardiotoxicity of local anesthetics occurred for bupivacaine, but not for L-N-n-propylpipecolic acid-2,6-xylidide.

Study of the action of lidocaine, bupivacaine and LEA on guinea-pig papillary muscle sodium channels Depression of cardiac conduction appears to be one of the primary mechanisms underlying local anesthetic cardiotoxicity. Depression of conduction by local anesthetics in both nerve and cardiac tissue results from a block of sodium channels. Furthermore, the degree of sodium channel block by local anesthetics is dependent upon the state of the sodium channel. Local anesthetic drugs typically have a high affinity for channels in the open or inactiviated states, but a very low affinity for channels in the rested state. Consequently, a block of sodium channels develops during the upstroke and plateau of the action potential and dissipates during the diastolic interval between beats. Since the effect of a local anesthetic is both state and time dependent, changes in both heart rate and diastolic membrane potential may alter drug action substantially.

In addition to sodium channel block, bupivacaine has a potent negative inotropic effect which may also contribute to its cardiotoxicity (Block and Covino, 1981; Courtney, 1984; Kotelko et al., 1984). The mechanism for this depression of the contractile response ought to be a depression of the transmembrane calcium current responsible for the triggering of the contractile apparatus. In order to initiate an investigation without the necessity to involve voltage-clamp of the calcium current, the preparations were subject to long depolarizing induced automaticity. If the cells are depolarized from about $-50$ to about $-30$ mV the automaticity is dependent on a transmembrane calcium current.

As has been mentioned above, bupivacaine has prominent cardiotoxic effects whereas lidocaine has much lower cardiotoxicity. LEA is compared with these two drugs regarding its effect on the cardiac sodium and calcium channels on a cellular level as outlined below.

Methods

Guinea pig papillary tests were carried out according to the recommendation of the "Report of the Subcommittee on Cardiotoxicity of Local Anesthetics" (Leroy D. Vandam, M.D., chairman). Guinea pig papillary muscle excised from the right ventricle were mounted in a single sucrose gap apparatus (Arlock & Katzune, 1985). Solutions maintained at 37° C.$\pm 0.5°$ continuously perfused the gap compartments. The rear chamber contained isotonic potassium chloride solution. The drugs were added to a Tris-Tyrode solution passing the tip of the muscle. The Tris-Tyrode solution contained (mM): NaCl, 145; KCl, 4; $CaCl_2$, 1.2; $MgCl_2$, 1.05; glucose, 5.5 Tris maleate, 5. It was adjusted to pH 7.4 with trismaleate and HCl before use and gassed with 100% oxygen. Isotonic sucrose solution isolated the rear from the tip to enable current- and voltage-clamping.

The muscles were depolarized with long current pulses (1500 msec). These current steps can induce automaticity or DIA (depolarization induced automaticity). The steps were adjusted so the preparations were depolarized to from $-50$ to $-30$ mV since that is in that range that calcium current conductance is initiated.

Results

The results are based on 35 experiments (LEA: 14, bupivacaine: 9 and lidocaine: 12). The results represent the mean from representative experiments. In the absence of drug, Vmax (maximum upstroke velocity of the action potential) recovers from inactivation with an exponential time constant of less that 30 msec at -90 mV (Gettes and Reuter, 1974). In the presence of drug, an additional slower exponential component representing recovery of drug-blocked channels can be observed. The time constant of this recovery process is different for channels blocked by different drugs. At $-90$ mV, channels blocked by lidocaine recover to 90% in 308 msec (S.E.M.$=0$, n$=3$)*, LEA in 2048 msec (S.E.M.$=217$, n$=7$) and bupivacaine 3561 msec. (S.E.M. 459, n$=7$). The fast component representing recovery of drug-free channels from inactivation was not measurable in the presence of 10 uM lidocaine, since virtually all channels were blocked by drug, and was usually ignored when defining the time course of recovery in the presence of bupivacaine or LEA since Vmax is measured only after a recovery interval greater than 100 msec. (The fast component is only present in the control; it disappears when drug is added.)

*S.E.M.$=$standard error of means. n$=$number of experiments.

TABLE 8

| | Reduction of Force of Contraction (%) at 1 Hz | | |
|---|---|---|---|
| | LEA | BUPIVACAINE | LIDOCAINE |
| $5 \times 10^{-6}$ M | 13.8, N = 8, S.E.M. = 4.7 | 45.1, N = 4, S.E.M. = 7.4 | 9.4, N = 6, S.E.M. = 5.3 |
| $10^{-5}$ M | 9.6, N = 10, S.E.M. = 3.4 | 41.7, N = 4, S.E.M. = 8.4 | 0, N = 2 |
| $10^{-4}$ M | 8, N = 2, S.E.M. = 2 | — | — |

The force of contraction was measured with a strain gauge transducer before and after the addition of the test compounds to the medium. The percent reduction in maximum force of contraction from the control was calculated. The force of contraction was only moderately diminished after LEA. In contrast even at 1 Hz bupivacaine had a pronounced depressant action (Table 8).

Comments

These results show that all three drugs act on the cardiac sodium channels in a use-dependent fashion. Lidocaine has the lowest potency at equimolar concentrations and bupivacaine the highest. The latter drug is a very potent blocker and has a very high affinity for the activated and inactivated channels.

Recovery from block after bupivacaine is very slow. LEA recovers faster but in contrast to bupivacaine recovery is very much enchanced at higher membrane potentials ($-100 - 120$ mV).

In the experiment with the high concentration of LEA, $10^{-4}$M for a short period, no attenuated excitability could be detected. Vmas was very depressed but recovered gradually and was fully recovered after 20 min. at a stimulus rate of 1 Hz. After this time the resting potential had increased to 113 mV.

At the two concentrations studied, LEA had very mild depressant actions on contractability in contrast to bupivacaine.

In summary, all three drugs depressed the sodium channels. Most important, for bupivacaine the recovery from block was very slow, whereas LEA and lidocaine recovered considerably faster. This was especially obvious at hyperpolarized levels ($-100 - -120$ mV).

The recovery from block after 25 min. washout after $10^{-4}$M LEA showed that the drug was readily eliminated from the tissue. A compound having a short washout is less toxic than a compound having a longer washout.

L-N-n-propylpipecolic acid-2,6-xylidide may be used as an injectable local anesthetic in the form of a water soluble salt. It may be used as the base in suppositories, or it may be used as a topical anesthetic by being blended into conventional solvents and carriers including thixotropic mixtures which form gels, or in a suspension, or it may be tableted in conjunction with conventional tableting materials.

Salts of L-N-propylpipecolic acid-2,6-xylidide may be made with the common mineral acids, aliphatic carboxylic acids, aromatic carboxylic acids and amino acids. Conventional safeguards must, of course, be used in respect to L-N-n-propylpipecolic acid-2,6-xylidide, such as the use of isotonic solutions when the anesthetic is employed as an injectable, e.g, contained in an injectable aqueous solution. Such isotonic solutions may be prepared from suitable salts, such as the water soluble chlorides of sodium, potassium, calcium and magnesium respectively, or the water soluble sulphates of sodium, potassium and magnesium.

Of course, the concentration of L-N-n-propylpipecolic acid-2,6-xylidide when administered as a local anesthetic will be regulated to avoid tissue irritation or toxic reaction effects while still providing an anesthetizing amount of the isomer to a patient needing local anesthesia. The regulation of the concentration of this anesthetic can be achieved by following conventional toxicity tests and protocols heretofore established for local anesthetics.

The present invention may be embodied in other specific forms without departing from the spirit or essential attributes thereof and, accordingly, reference should be made to the appended claims, rather than to the foregoing specification, as indicating the scope of the invention.

We claim:

1. A method for inducing local anesthesia comprising administration to a patient needing local anesthesia an anesthetizing amount of the substantially pure L-isomer of N-n-propylpipecolic acid-2,6-xylidide or its water soluble salts substantially devoid of the racemic and the D-isomer of N-n-propylpipecolic acid-2,6-xylidide.

2. A method according to claim 1 wherein the pure L-isomer of N-n-propylpipecolic acid-2,6-xylidide or its water soluble salts is contained in an injectable aqueous solution.

3. Substantially pure L-isomer of N-n-propylpipecolic acid-2,6-xylidide, and its water soluble salts, substantially devoid of racemic and D-N-n-propylpipecolic acid-2,6-xylidide.

4. The method of inducing local anesthesia in humans by the application of the compound of claim 3 to the region intended to be anesthetized in a concentration sufficient to effect anesthesia, and below that which would confer an adverse toxic reaction.

5. An injectable local anesthetic composition comprising an aqueous solution containing a sufficient amount of a water soluble salt of the compound of claim 3 to induce local anesthesia in humans, but with the concentration being below that which would confer an adverse toxic reaction.

6. A topical local anesthetic composition comprising a carrier and the compound of claim 3.

* * * * *

UNITED STATES PATENT AND TRADEMARK OFFICE
CERTIFICATE OF CORRECTION

PATENT NO. : 4,695,576
DATED : September 22, 1987
INVENTOR(S) : Bo T. af Ekenstam, et al.

It is certified that error appears in the above—identified patent and that said Letters Patent is hereby corrected as shown below:

On the title page, Item [73] "Astra Lake Medel Aktiebolag," to --Astra Lakemedel Aktiebolag,--

Column 1, Line 25, change "pipecolicacaid" to --pipecolic-acid--

Column 9, Line 17, change "bdrenaline" to --adrenaline--

Signed and Sealed this

Twenty-sixth Day of April, 1988

Attest:

DONALD J. QUIGG

*Attesting Officer*         *Commissioner of Patents and Trademarks*